US00PP10040P

United States Patent [19]

Polys

[11] Patent Number: Plant 10,040

[45] Date of Patent: Sep. 23, 1997

[54] CHRYSANTHEMUM PLANT NAMED 'SANDY DAVIS'

[75] Inventor: Susan M. Polys, Salinas, Calif.

[73] Assignee: Yoder Brothers, Inc., Barberton, Ohio

[21] Appl. No.: 605,612

[22] Filed: Feb. 22, 1996

[51] Int. Cl.[6] ..... A01H 5/00

[52] U.S. Cl. ..... Plt./82.3

[58] Field of Search ..... Plt./82.2, 82.3

[56] References Cited

U.S. PATENT DOCUMENTS

| | | | |
|---|---|---|---|
| P.P. 8,295 | 7/1993 | VandenBerg | Plt./82.3 |
| 4,616,099 | 10/1986 | Sparkes | 47/58 |

OTHER PUBLICATIONS

Broertjes, et al., 1980, "A mutant of a mutant of a . . . Irradiation of Progressive radiation–induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd. pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp.27–29, 320–327.

Chan, 1966, "Chrysanthemum and rose mutations induced by x–rays", Am. Soc. Hort. Sci. Proc., pp. 613–620.

Broertjes, 1966, "Mutation breeding of chrysanthemums", Euphytica, 15;156–162.

Dowrick, et al., 1966, "The induction of mutations in chrysanthemum using x–and gamma radiation," Euphytica, 15:205–210.

*Primary Examiner*—Howard J. Locker
*Attorney, Agent, or Firm*—Foley & Lardner

[57] ABSTRACT

A Chrysanthemum plant named Sandy Davis particularly characterized by its flat capitulum flat capitulum form; daisy capitulum type; yellow-orange ray floret color; diameter across face of capitulum of 64 to 70 mm when fully opened, when grown as a pinched spray pot mum; photoperiodic flowering response of 58 to 63 days after start of short days; plant height, with 14 long days after sticking unrooted cuttings and with 1 to 2 applications of 2500 ppm B-9 SP ranges from 20 to 25 cm when grown as a pinched pot mum with 4 cuttings in a 15 cm pot; spreading branching pattern, each plant having 4 to 6 laterals after pinch; and recommended as a spray pot mum.

1 Drawing Sheet

The present invention comprises a new and distinct cultivar of Chrysanthemum, botanically known as *Dendranthema grandiflora*, and referred to by the cultivar name Sandy Davis.

Sandy Davis, identified as 4498 (84-382H03), is a product of a mutation induction program. The new cultivar was discovered and selected by inventor Susan M. Polys on Aug. 29, 1991 in a controlled environment in Salinas, Calif. as one flowering plant within a flowering block established as rooted cuttings from stock plants which had been exposed as unrooted cuttings to an X-ray source of 1750 rads in Fort Myers, Fla. Mar. 20, 1991. The irradiated parent cultivar was the cultivar Orange Davis, disclosed in U.S. Plant Pat. No. 8,295 and described as a flat daisy spray pot mum with orange-bronze flower color.

The irradiation program resulting in Sandy Davis had as its primary objective the expansion of color ranges of the cultivar Davis, disclosed in U.S. Plant Pat. No. 7,325, and the parent cultivar Orange Davis. The irradiation program comprised irradiation of cuttings of the parent cultivar at irradiation levels of 1500, 1750 and 2000 rads. A total of 1529 cuttings harvested from a total of 225 irradiated plants were planted on Jul. 8, 1991. Of these, 9 initial selections were made, which selections were then revegetated and reflowered. Three consecutive flowerings resulted in discarding all of the original 9 selections on May 1, 1992. Two codes were reselected prior to discarding the original code, and were maintained as PIs (Possible Introductions) and further trialed in Salinas, Calif. and Leamington Ontario, Canada, ultimately resulting in discarding one code on Oct. 11, 1994 and the decision to introduce the one remaining selection as Sandy Davis.

The first act of asexual reproduction of Sandy Davis was accomplished when vegetative cuttings were taken from the initial selection in November of 1991 in a controlled environment in Salinas, Calif. by technicians working under supervision of Susan M. Polys.

Horticultural examination of controlled flowerings of successive plantings has shown that the unique combination of characteristics as herein disclosed for Sandy Davis are firmly fixed and are retained through successive generations of asexual reproduction.

Sandy Davis has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Leamington, Ontario, Canada, under greenhouse conditions which approximate those generally used in commercial greenhouse practice.

The following traits have been repeatedly observed and are determined to be basic characteristics of Sandy Davis, which, in combination, distinguish this Chrysanthemum as a new and distinct cultivar:

1. Flat capitulum form.
2. Daisy capitulum type.
3. Yellow-orange ray floret color.
4. Diameter across face of capitulum of 64 to 70 mm when fully opened, when grown as a pinched spray pot mum.
5. Photoperiodic flowering response of 58 to 63 days after start of short days.
6. Plant height, with 14 long days after sticking unrooted cuttings and with 1 to 2 applications of 2500 ppm B-9 SP ranges from 20 to 25 cm when grown as a pinched pot mum with 4 cuttings in a 15 cm pot.

7. Branching pattern is spreading, each plant having 4 to 6 laterals after pinch.

8. Recommended as a spray pot mum.

The accompanying photographic drawing is a side view of Sandy Davis, grown as a spray pot mum with 4 cuttings in a 15 cm pot, with the colors being as nearly true as possible with illustrations of this type.

Of the commercial cultivars known to the inventor, the most similar in comparison to Sandy Davis is the parent cultivar Orange Davis. All traits of Sandy Davis are similar to those of Orange Davis, except for the ray floret color and the flowering response to short days. The ray floret color of Sandy Davis (RHS 22A to 24B) is significantly lighter than the ray floret color of Orange Davis (RHS 34B, tinged with 178C to 179A). The flowering response to short days of Sandy Davis is 1 to 2 days slower than the flowering response of Orange Davis.

In the following description color references are made to The Royal Horticultural Society Colour Chart. The color values were determined on plant material grown as a pinched pot mum with 4 cuttings in a 15 cm pot in Salinas, Calif. on May 22, 1995.

Classification

*Botanical.*—*Dendranthema grandiflora* cv Sandy Davis.

*Commercial.*—Flat daisy spray pot mum.

INFLORESCENCE

A. Capitulum:

*Form.*—Flat

*Type.*—Daisy.

*Diameter across face.*—64 to 70 mm when fully opened.

B. Corolla of ray florets:

*Color (general tonality from a distance of three meters).*—Yellow-orange.

*Color (upper surface).*—22A to 24B.

*Color (under surface).*—22A to 24B.

*Shape.*—Straight, oblong, slightly ribbed.

C. Corolla of disc florets:

*Color (mature).*—9A.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—20 to 25 cm when grown as a pinched pot mum with 14 long days after sticking unrooted cuttings prior to start of short days and with 1 to 2 applications of 2500 ppm B-9 SP.

*Branching pattern.*—Spreading, with 4 to 6 laterals after pinch.

B. Foliage:

*Color (upper surface).*—147A.

*Color (under surface).*—147B.

*Shape.*—Deeply lobed and serrated.

What is claimed is:

1. A new and distinct Chrysanthemum plant named Sandy Davis, as described and illustrated.

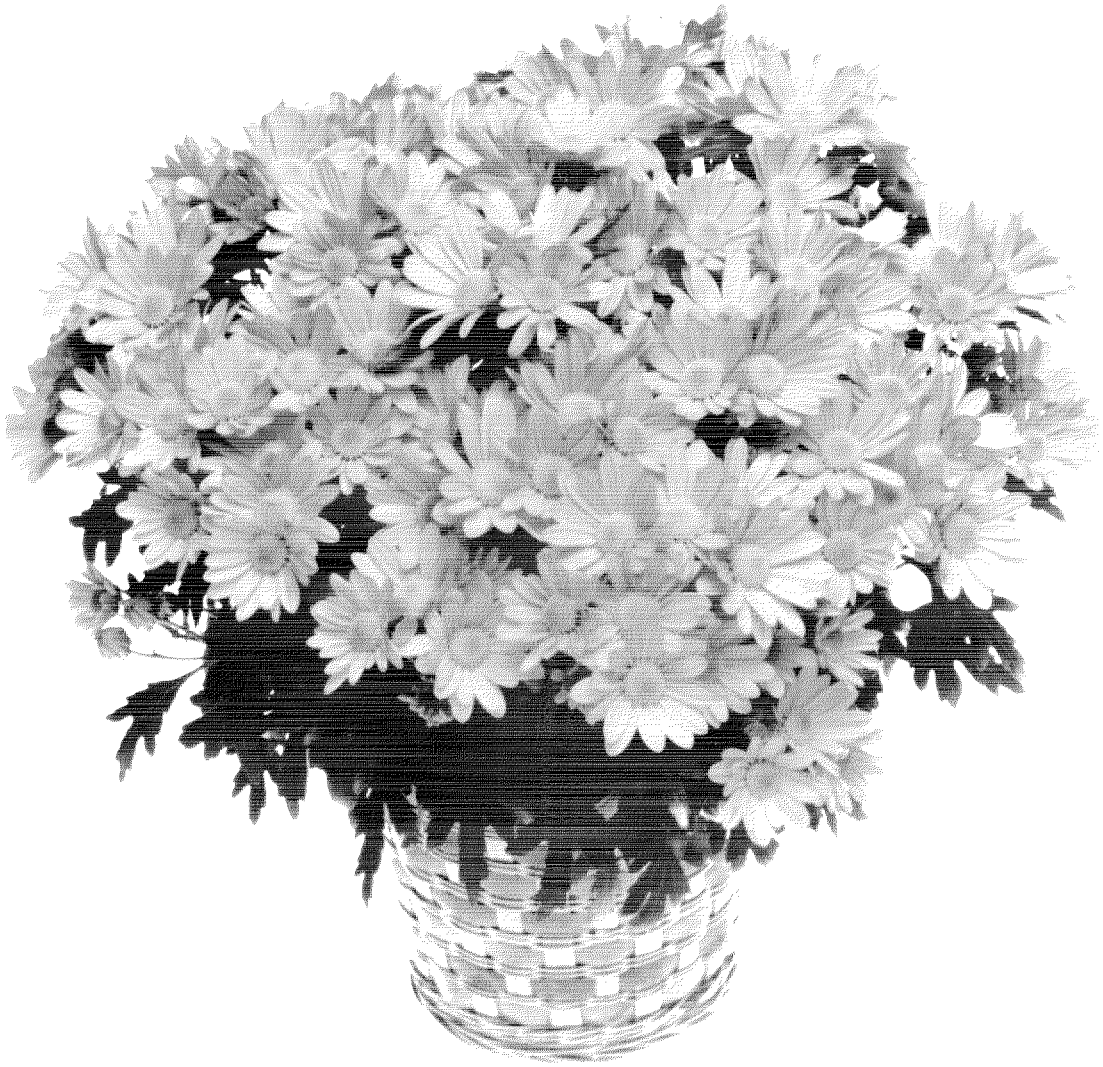

* * * * *